United States Patent [19]
Knox et al.

[11] Patent Number: 5,814,003
[45] Date of Patent: Sep. 29, 1998

[54] PULSATILE ANTI-EMBOLISM STOCKING

[75] Inventors: Samuel M. Knox; Michael R. Griffin, both of Hickory, N.C.

[73] Assignee: Alba-Waldensian, Inc., Valdese, N.C.

[21] Appl. No.: 697,982

[22] Filed: Sep. 4, 1996

[51] Int. Cl.$^6$ ........................................................ A61F 5/00
[52] U.S. Cl. ................................................. 602/63; 2/239
[58] Field of Search ........................... 602/61–63, 13; 601/149–152; 2/239

[56] References Cited

U.S. PATENT DOCUMENTS

| | | |
|---|---|---|
| 3,826,249 | 7/1974 | Lee et al. . |
| 3,975,929 | 8/1976 | Fregeolle . |
| 3,999,406 | 12/1976 | Boeckle et al. . |
| 4,390,999 | 7/1983 | Lawson et al. . |
| 5,022,387 | 6/1991 | Hasty . |
| 5,407,421 | 4/1995 | Goldsmith ............................. 602/13 X |

*Primary Examiner*—Linda C. Dvorak
*Attorney, Agent, or Firm*—Bell Seltzer Intellectual Property Law Group of Alston & Bird, LLP

[57] ABSTRACT

A stocking for use in positioning a pulsatile bladder about a portion of a user's body is described. The stocking is desirably circularly knit to have an inner sleeve, and an outer sleeve extending concentrically over the inner sleeve. The inner sleeve desirably is knit to provide a graduated degree of compression along the underlying portion of a person's body when the stocking is positioned on a wearer's limb. The outer sleeve is preferably relatively less elastic than the inner sleeve, so as to prevent a bladder positioned within the stocking from pressing uncomfortably into a wearer's flesh. The outer sleeve also desirably includes first and second spaced-apart openings, one for bladder insertion and the other for allowing the exit of tubing typically associated with pulsatile bladders. The stocking is preferably integrally knit on a circular knitting machine such that it comes off of the machine in finished form.

17 Claims, 2 Drawing Sheets

PULSATILE ANTI-EMBOLISM STOCKING

BACKGROUND OF THE INVENTION

1. Field of the Invention

The invention generally relates to a pulsatile anti-embolism stocking. More specifically, the invention relates to a pulsatile anti-embolism stocking which can be produced in finished form on a circular knitting machine.

2. Description of the Prior Art

Persons having restricted mobility due to injury or infirmity are often faced with additional physical problems as a result of their lack of movement. For example, decreased circulation resulting from lack of movement can cause the formation of air bubbles or clots in a person's blood vessels. Such emboli can be life threatening, as they can occlude the blood vessels and/or travel to the heart or brain, with serious or fatal results. Similarly, decreased circulation can cause death or decay of tissue (e.g. gangrene) which in severe cases, can require removal of the affected limb.

To avoid such consequences, doctors often provide their bedridden or movement restricted patients with devices which reduce the tendency of emboli to form. For example, commonly assigned U.S. Pat. No. 3,975,929 to Fregeolle describes a circularly knit anti-embolism stocking which provides a graduated compressive force along the leg of a wearer. The stocking of the Fregeolle patent is described as being thigh length and including a leg portion having an extension formed of partial courses extending upwardly therefrom around a portion of the stocking circumference, and an elastic band extending from one side of the extension to the other and around the remaining stocking circumference. The knit structure is also described as being modified along the length of the stocking in order to provide graduated compression therealong.

Another device which is designed to improve circulation is the pulsatile bladder. Such bladders are designed to be positioned proximate a portion of a user's body where circulation is to be improved (typically on a limb), and a fluid such as air is pumped through the thus-positioned bladder in a pulsating manner to increase circulation of blood through the underlying blood vessels in the limb. In order to maintain the pulsatile bladder in the desired position on a wearer's body it must be secured in some manner, preferably by one which is comfortable to the wearer. One method of securing such a bladder to a wearer's body is by way of a specially designed stocking adapted to accommodate and retain the bladder in position.

Stockings adapted to accommodate a pulsatile bladder typically include a knitted tubular calf-covering member, to which a foot covering member is secured. Such stockings generally include a substantially rectangular piece of fabric having a first longitudinal side secured along the length of the calf-covering member, and a substantially free second longitudinal side. A first half of a zipper is secured along the length of the second longitudinal side of the rectangular piece of fabric, with the mating zipper half being secured along the length of the calf-covering member in a spaced relationship to the first longitudinal side of the rectangular piece of fabric. In this way, when the zipper is zipped together, the piece of fabric wraps around a major portion of the calf-covering member in a layered relationship therewith. The substantially rectangular piece of fabric is also typically folded inwardly (i.e. towards the calf-covering member) along its widthwise-extending sides, so as to form pockets along the upper and lower sides of the piece of fabric. In this way, the pockets can retain a pulsating bladder between the substantially rectangular piece of fabric and the tubular calf-covering member, such that it can encourage blood flow through the blood vessels of a wearer's underlying leg. In addition, a button hole-type opening is generally located proximate a lower end of the piece of fabric, for allowing tubing associated with the bladder to extend therethrough outwardly from the bladder pocket.

Because these conventional pulsatile bladder-retaining stockings require seaming of the zipper halves in the appropriate location, seaming of the piece of fabric to the calf-covering member, and the formation of ravel-stop means along all of the raw edges of the pieces of material, the amount of labor involved in their production tends to be very high. As a result, such stockings tend to be very costly to manufacture. Further, positioning of a pulsating bladder with respect to such a stocking and a user's body is limited, since the bladder pocket does not extend around the entire circumference of the stocking. In other words, the bladder must necessarily be positioned at a specific predetermined location on the stocking, which depends upon the positioning of the piece of fabric with respect to the calf-covering member. In addition, the zipper can tend to bear against the wearer's leg, causing discomfort or irritation thereto.

Thus a need exists for a means for securing a pulsatile bladder to a wearer's body which is inexpensive to manufacture, comfortable to the wearer, and which allows good positioning of the pulsatile bladder with respect to the user's body.

SUMMARY OF THE INVENTION

With the foregoing in mind, it is an object of the present invention to provide a stocking for stably and comfortably securing a pulsatile bladder to a user's body which requires only a minimal number of production steps.

It is also an object of the present invention to provide a method for manufacturing a stocking for securing a pulsatile bladder to a wearer's body using only a minimal number of manufacturing steps.

It is a further object of the invention to provide a system for reducing the formation of emboli which is effective and comfortable, and which requires only a minimal number of manufacturing steps.

In accordance with these objectives, the invention relates to a circularly knit, pulsatile anti-embolism stocking (hereinafter "PAE stocking") which comes off of the knitting machine in substantially finished form, and a method for making such a stocking. The stocking desirably includes an inner tubular sleeve and an outer tubular sleeve which is relatively less elastic than the inner sleeve, and which extends coextensively about the inner sleeve. In a preferred form of the invention, the inner and outer tubular sleeves are secured together about their respective upper and lower ends, to define a cylindrically-shaped pocket region therebetween. In a particularly preferred form of the invention, the inner and outer sleeves are integrally knit together such that their respective ends are secured together during the knitting process, without the need for additional processing steps. In a further preferred form of the invention, the inner sleeve is knit such that it will provide graduated compression along the length of the appendage onto which the stocking is positioned. This graduated compression can be formed by modifying the stitch structure, stitch length, yarn feed, or by other conventional methods.

The outer relatively less elastic sleeve desirably includes first and second pocket access openings. In this way, a pulsatile bladder can be positioned within the pocket region between the inner and outer sleeves by inserting it through one of the openings, while the second opening can allow the exit of tubing typically associated with such bladders. In a preferred form of the invention, the bladder insertion opening is located proximate the upper end of the outer sleeve, while the tubing opening is relatively smaller than the insertion opening and is located proximate the lower end of the outer sleeve. One or more transitional courses desirably join the lower ends of the inner and outer sleeves; these courses are preferably made from a fusible yarn, which upon heating, fuses together and further stabilizes this juncture of the inner and outer sleeves.

A preferred method of constructing a PAE stocking according to the instant invention involves knitting at least one course of transfer stitches on a first needle bed of a circular knitting machine, and knitting a second series of courses on the opposite needle bed of the knitting machine for a predetermined number of courses. At a predetermined position in that section of courses, a small number of the needles on the bed are taken out of action for a few courses to form a small number of held stitches, which form a small opening in the tubular fabric. All of the needles are then brought back into action and another elongate tubular section is knit. At a second predetermined position on that section of courses, a number of needles are again taken out of action for several courses to form a series of held stitches which form a second opening in the tubular fabric. The needles are again brought into action as the machine continues knitting a tubular structure. At a predetermined position, the knitting process is desirably modified to form a region having a greater amount of elasticity than the previously produced tubular structure (e.g. by inlaying an elastic yarn, changing the stitch structure, or the like.) This region of greater elasticity desirably forms an upper section of the outer sleeve and the inner sleeve of the stocking structure. Once the desired number of courses have been knit to form the inner sleeve, the original series of transfer stitches is transferred from the first needle bed to the other needle bed to join the inner and outer layers together at their respective lower ends.

A small number of courses are desirably then knit to form a transitional region, to which a band or foot portion can then be knit. In a particularly preferred form of the invention, at least a portion of the transitional stitches include a fusible yarn (e.g. a heat fusible yarn.) In this way, the finished stocking can be heated to fuse the fusible yarn, which melds with the other yarns in the transitional region to provide a reinforced region at the juncture of the inner and outer sleeves. This reinforced region serves to increase stocking durability and reduce the incidence of raveling which can occur following repeated launderings. A heat fusible yarn is particularly preferred for use in stockings which are adapted to be scoured after production, as the scouring process itself can serve to fuse the fusible yarn without the need for additional production steps.

DETAILED DESCRIPTION OF THE PREFERRED EMBODIMENTS

The present invention will now be described more fully hereinafter with reference to the accompanying drawings, in which a preferred embodiment of the invention is shown. This invention may, however, be embodied in many different forms and should not be construed as limited to the embodiments set forth herein; rather, this embodiment is provided so that this disclosure will be thorough and complete and will fully convey the scope of the invention to those skilled in the art. Like numbers refer to like elements throughout.

Figure 1:
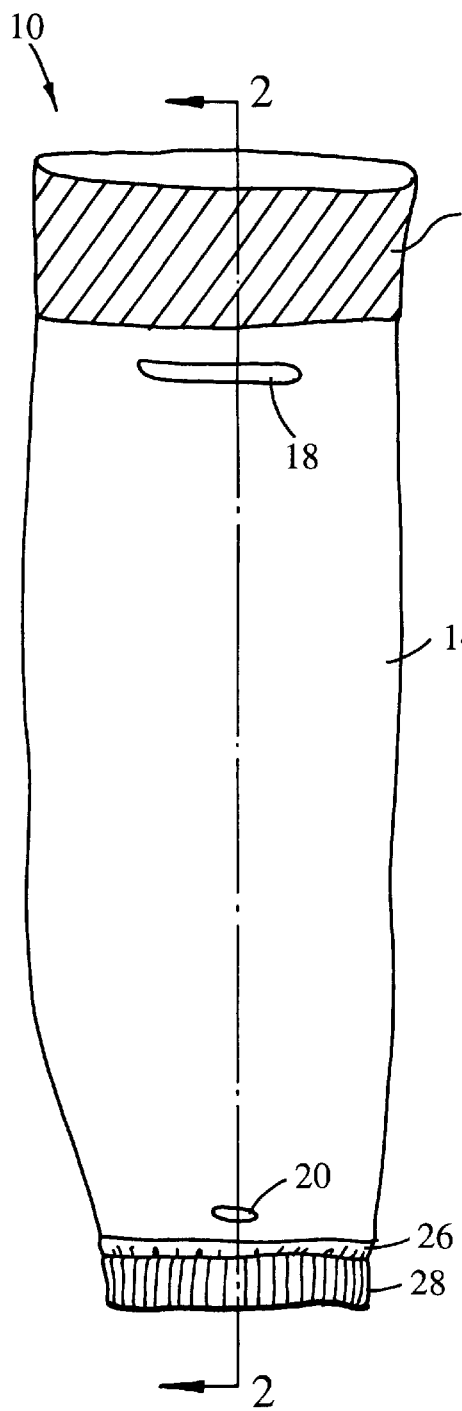
FIG. 1 is a perspective view of an embodiment of a pulsatile anti-embolism stocking made according to the present invention.
Figure 2:
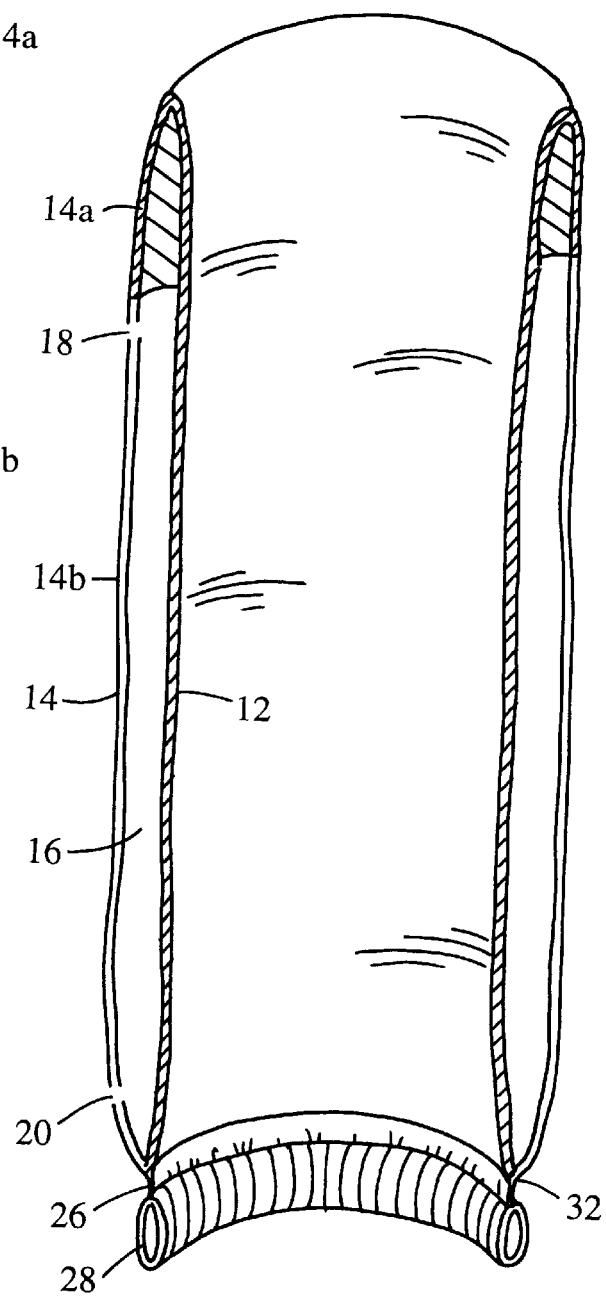
FIG. 2 is a cross-sectional view of the stocking shown in FIG. 1, as taken along line 2—2.
Figure 3:
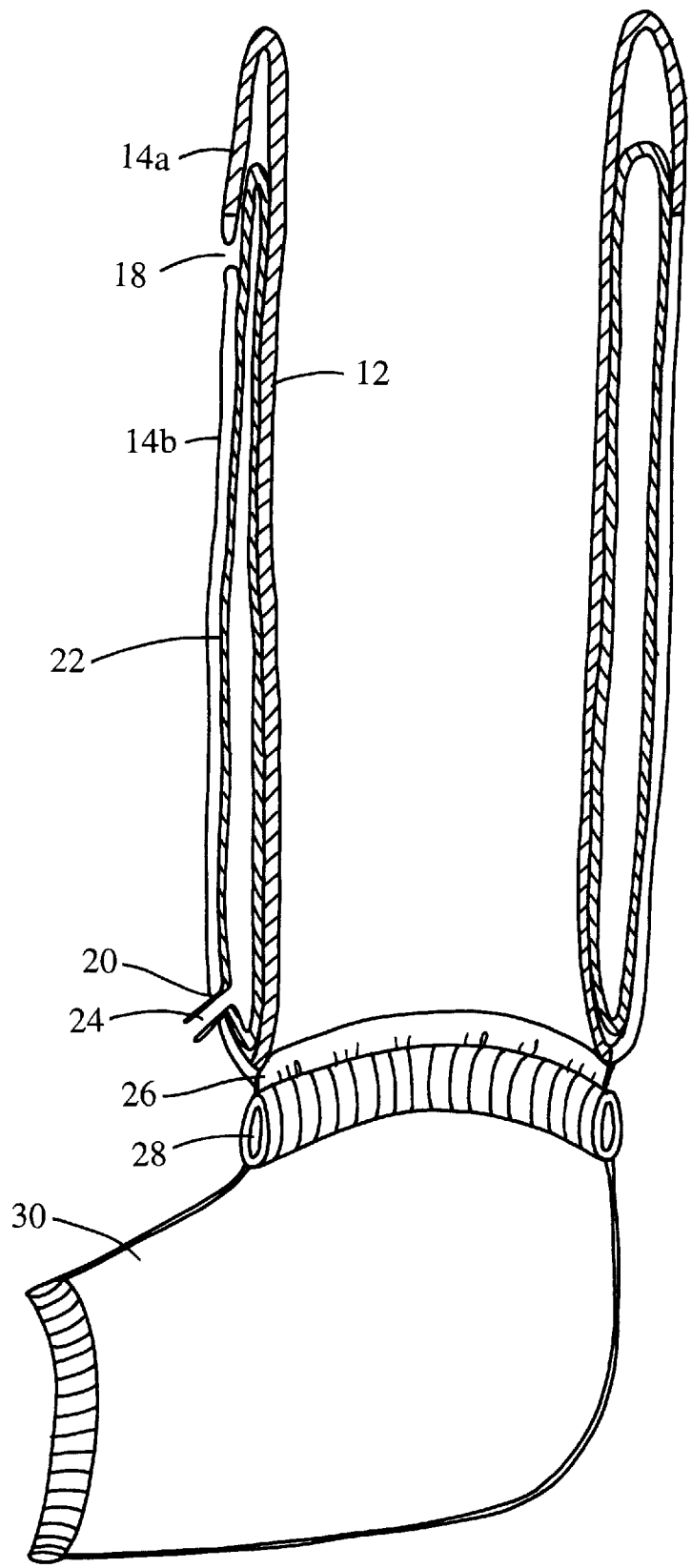
FIG. 3 is a cross-sectional view of an embodiment of a stocking according to the instant invention similar to that of FIG. 2, as it would appear with a pulsatile bladder positioned within the pocket between the inner and outer sleeves and a foot portion secured to the stocking lower end.

With reference to the attached drawings, FIG. 1 illustrates one embodiment of a stocking according to the invention, and FIG. 2 is a cross-sectional view of the stocking shown in FIG. 1, as it appears prior to insertion of a pulsatile bladder, and FIG. 3 shows a cross-sectional view of an embodiment like that of FIGS. 1 and 2, as it would appear with an attached foot portion and a pulsatile bladder positioned within the pocket. The stocking, shown generally at 10, desirably includes inner 12 and outer 14 tubular sleeves which are adapted to extend along the length of a wearer's limb (e.g. the calf of the leg). The inner and outer sleeves 12, 14 are desirably secured together along their upper and lower ends to form a hollow pocket 20 therebetween. In a preferred form of the invention, the inner and outer sleeves 12, 14 are integrally knit together so as to require no further manufacturing steps, in a manner discussed further herein.

The inner sleeve 12 is desirably knit so as to be more elastic than the outer sleeve 14, so that it can fit closely and snugly around a wearer's limb. In a preferred form of the invention, the inner sleeve 12 is knit so that the degree of compression is graduated along the sleeve length to conform to the contours of a wearer's limb. This can be done using conventional methods such as feeding or inlaying varying amounts of elastic material, varying the stitch length or structure, or the like. In a particularly preferred form of the invention, the same knit stitch structure is used on the inner and outer sleeves 12, 14, but an elastic yarn such as spandex is laid into the courses forming the inner sleeve.

The outer relatively less elastic sleeve 14 desirably includes a relatively small upper section 14a which has a greater elasticity than the major portion 14b of the outer sleeve. In this way, the relatively more elastic upper section 14a can assist in maintaining the stocking in its desired position on the wearer's body. The outer sleeve 14 also desirably includes a first opening 18 proximate its upper end and a second relatively smaller opening 20 proximate its lower end. In this way, a pulsatile bladder 22 can be inserted through the relatively larger first opening 18 into the pocket 16 between the inner and outer layers, and the tubing 24 which typically extends from such a bladder can extend outwardly through the second opening 20. Further, because the outer layer 14 is less elastic than the inner layer 12, the tendency for the bladder 22 to be pressed uncomfortably against a wearer's limb by the stocking 10 is reduced. Additionally, because the pocket 16 formed between the inner and outer tubular layers 12, 14, desirably extends continuously around the entire circumference of the stocking 10, the position of the bladder 22 on the wearer's leg can be adjusted as desired so that it can be positioned at virtually any location about the circumference of a wearer's limb.

The inner and outer layers 12, 14 are desirably secured together proximate their lower ends, with a number of courses of transitional stitches 26 extending downwardly from the juncture of the inner and outer layers. The stocking 10 can terminate in a turned welt 28, as illustrated, or a partial or full foot portion 30 can be knit thereto.

The knitting process, in one embodiment of the invention, can be performed as follows, with reference to FIG. 2. A first course or series of courses 32 (i.e., the transfer stitches) can be knit on one of the sets of needles on a circular knitting machine, e.g., the dial needles. A second series of courses is then knit on the opposite set of needles (e.g., the cylinder needles) for a predetermined, relatively small length, which will form the lower end section of the outer sleeve 14. A number of stitches are held for a set number of courses, e.g., by taking a number of needles out of action, to form the small opening 20. The machine continues knitting, with the held needles being put back into service, to form a tubular body which forms a major portion of the length of the outer sleeve 14. At a preselected point, a number of needles are again taken out of commission for a number of courses to form the larger opening 18. By forming the first and second openings in this way, further finishing of them is not required as they do not have a tendency to ravel.

The machine continues knitting to form the upper portion 14a of the outer sleeve 14, and preferably the structure of this portion is modified to render it more elastic than the major portion 14b of the outer sleeve. In a particularly preferred method, an elastic yarn such as spandex is laid in along this upper portion to assist in the stocking's securement about a wearer's limb. The elastic yarn continues to be laid in as the machine continues knitting a tubular body which forms the stocking inner sleeve 12. The inner sleeve 12 is knit such that it provides graduated compression, in order to form a stocking 10 which accommodates the curved shape of a wearer's leg.

Once the desired number of courses have been knit to form the inner sleeve 12, the original series of stitches 32 (i.e., the transfer stitches) is transferred from the dial needles to the cylinder needles to join the inner and outer sleeves 12, 14 together. A small number of courses are then subsequently knit to form transitional region 26, to which is then knitted a band 28 in the form of a turned welt. As stated previously, the stocking could include a partial or full foot covering portion such as that illustrated at 30 in FIG. 3 in addition to or instead of an elastic band 28, as illustrated in FIG. 2.

The stocking 10 thus comes off the machine in finished form. To conform with medical guidelines, the stocking 10 is desirably scoured for sterility purposes. In one form of the invention, a course or two proximate the junctures of the transitional stitches with the sleeve lower ends and/or the band 28 can be knit from a fusible yarn. In this way, when the invention is scoured, the heat from the scouring process fuses the yarns together to make a high strength connection between the courses which can reduce the incidence of raveling and juncture weakening. It is noted that the method can be reversed such that the transfer stitches are knit on the cylinder rather than the dial needle bed of the machine, or the knitting order can be modified, within the scope of the present invention, as will be appreciated by those having ordinary skill in the art.

In the drawings and the specification, there has been set forth preferred embodiments of the invention and, although specific terms are employed, the terms are used in a generic and descriptive sense only and not for the purpose of limitation, the scope of the invention being set forth in the following claims.

It is claimed:

1. A stocking for securing a pulsatile bladder to a person's body comprising:
    a circularly knit tubular outer sleeve having upper and lower circumferential ends, and
    a circularly knit tubular inner sleeve including upper and lower circumferential ends, said inner sleeve being positioned within said outer sleeve and having its upper end secured to said outer sleeve proximate the upper end thereof and its lower end secured to said outer sleeve proximate the lower end thereof to define a cylindrically shaped pocket therebetween, and said outer sleeve including an opening for enabling a pulsatile bladder to be operatively positioned within said pocket.

2. The stocking according to claim 1, wherein said opening in said outer sleeve is located proximate the upper end of the outer sleeve and further comprising a second relatively smaller opening proximate the lower end of said outer sleeve for enabling tubing associated with a pulsatile bladder to extend outwardly from said pocket.

3. The stocking according to claim 1, further comprising a circular band secured proximate the lower ends of said inner and outer sleeves, for encircling a wearer's limb.

4. The stocking according to claim 3, wherein said circular band comprises a series of courses integrally knit with the inner and outer sleeves in the form of a turned welt.

5. The stocking according to claim 1, further comprising a series of transitional stitches integrally knit between lower ends of said inner and outer sleeves and said circular band.

6. The stocking according to claim 5, wherein said transitional stitches comprise a fusible yarn for reinforcing a juncture of said lower edges and circular band.

7. The stocking according to claim 1, wherein said inner and outer sleeves are integrally knit together in the form of an enlarged turned welt.

8. The stocking according to claim 1, wherein said inner sleeve is relatively more elastic than said outer sleeve, for providing a close fit about a wearer's limb.

9. The stocking according to claim 1, wherein an upper portion of said outer sleeve is relatively more elastic than a lower portion of said outer sleeve, to assist is the securement of the stocking about a wearer's limb.

10. The stocking according to claim 1, wherein said inner sleeve has varying elasticity along its length, to thereby provide graduated compression to a wearer's limb.

11. A system for reducing the formation of emboli in a person comprising:
    a stocking including a circularly knit tubular outer sleeve having upper and lower circumferential ends and a circularly knit tubular inner sleeve including upper and lower circumferential ends, said inner sleeve being positioned within said outer sleeve and having its upper end secured to said outer sleeve proximate the upper end thereof and its lower end secured to said outer sleeve proximate the lower end thereof to define a cylindrically shaped pocket therebetween, and
    a pulsatile bladder positioned within said pocket, for providing a pulsating force to a region of a wearer's body underlying said inner sleeve.

12. The system according to claim 11, wherein one of said inner and outer sleeves includes at least one opening and tubing associated with said pulsatile bladder extends outwardly from said pocket through said opening.

13. The system according to claim 12, wherein said opening comprises a plurality of held knit stitches.

14. The system according to claim 11, further comprising a foot portion for securing the stocking to a wearer's foot.

15. The system according to claim 11, wherein said inner and outer sleeves of said stocking are integrally knit together.

16. The system according to claim 11, wherein said inner sleeve has varying elasticity along its tubular length to thereby provide graduated compression to portions of a wearer's body positioned within the inner sleeve when the system is worn.

17. The system according to claim 11, wherein said inner sleeve is relatively more elastic than the outer sleeve, to thereby provide a close fit of the stocking without pressing the bladder uncomfortably into a portion of a wearer's body positioned within the stocking when the system is worn.

* * * * *